US008106050B2

(12) United States Patent
Meijer et al.

(10) Patent No.: US 8,106,050 B2
(45) Date of Patent: Jan. 31, 2012

(54) DERIVATIVES OF PYRROLO-PYRAZINES HAVING A KINASE INHIBITORY ACTIVITY AND THEIR BIOLOGICAL APPLICATIONS

(75) Inventors: Laurent Meijer, Roscoff (FR); Jean-Michel Vierfond, Maisons Alfort (FR); Yvette Mettey, Poitiers (FR)

(73) Assignee: Centre National de la Recherche Scientifique (C.N.R.S.), Paris Cedex (FR)

( * ) Notice: Subject to any disclaimer, the term of this patent is extended or adjusted under 35 U.S.C. 154(b) by 1344 days.

(21) Appl. No.: 10/524,044

(22) PCT Filed: Aug. 8, 2003

(86) PCT No.: PCT/EP03/09515
§ 371 (c)(1),
(2), (4) Date: Dec. 12, 2005

(87) PCT Pub. No.: WO2004/016614
PCT Pub. Date: Feb. 26, 2004

(65) Prior Publication Data
US 2008/0161312 A1 Jul. 3, 2008

(30) Foreign Application Priority Data
Aug. 9, 2002 (EP) .................................. 02292019

(51) Int. Cl.
*A01N 43/58* (2006.01)
*A01N 43/60* (2006.01)
*A01N 43/38* (2006.01)
*A61K 31/50* (2006.01)
*A61K 31/495* (2006.01)
*A61K 31/4965* (2006.01)
*A61K 31/40* (2006.01)

(52) U.S. Cl. .................... 514/249; 514/255.05; 514/412; 544/350; 548/453

(58) Field of Classification Search ................ 514/183, 514/249, 255.05, 412; 544/350; 548/453
See application file for complete search history.

(56) References Cited

U.S. PATENT DOCUMENTS

| 5,286,860 | A | 2/1994 | Blum et al. | |
|---|---|---|---|---|
| 6,528,509 | B1 | 3/2003 | Hale | |
| 6,943,174 | B2 * | 9/2005 | Picard et al. | 514/300 |
| 2004/0106624 | A1 | 6/2004 | Guizi | |
| 2009/0048260 | A1 | 2/2009 | Becq | |

FOREIGN PATENT DOCUMENTS

| EP | 1388541 A | 2/2004 |
|---|---|---|
| WO | 95/33752 A | 12/1995 |
| WO | 98/22457 A | 5/1998 |
| WO | 99/20624 A | 4/1999 |
| WO | 99/65908 A | 12/1999 |
| WO | 99/65909 A | 12/1999 |
| WO | 00/17202 A | 3/2000 |
| WO | 00/71129 A | 11/2000 |
| WO | 01/42246 A | 6/2001 |
| WO | 01/47922 A | 7/2001 |
| WO | 01/96336 A | 12/2001 |
| WO | 02/00661 A | 1/2002 |
| WO | 03/089434 A | 10/2003 |
| WO | 2004/032874 A | 4/2004 |

OTHER PUBLICATIONS

Davis et. al., Tetrahedron, 1992, Pergamon Press, vol. 48, pp. 939-952.*
International Search Report of PCT/EP03/09515 dated Feb. 17, 2004.
Doble, B. W. et al., "GSK-3: Tricks of the trade for a multi-tasking kinase", Journal of Cell Science, Apr. 1, 2003, United Kingdom, vol. 116, No. 7, pp. 1175-1186, XP 002326404,ISSN: 0021-9533.
Kunick, Conrad et al., "I-Azakenpaullone is a selective inhibitor of glycogen synthase kinase-3β", Bioorganic & Medicinal Chemistry Letters, Jan. 19, 2004, vol. 14, No. 2, pp. 41 3-31 6, XP002326403, ISSN: 0960-894X.
Meijer, L. et al., "Pharmacological inhibitors of glycogen synthase kinase 3", Trends in Pharmacological Sciences 2004, United Kingdom, vol. 25, No. 9, pp. 471-480, XP002326405,ISSN: 01 65-61 47.
Mettey, Y. et al., "Aloisines, a new family of CDK/GSK-3 Inhibitors. SAR Study, crystal structure in complex with CDK2, enzyme selectivity, and cellular effects", Journal of Medicinal Chemistry, American Chemical Society, Washington, US, vol. 46, No. 2, Dec. 18, 2002, pp. 222-236, XP002285187, ISSN: 0022-2623.
B.A.J. Clark et al., "Formation of Certai Substituted 5H-Pyrrolo [2,3-b]pyrazines by Thermal Cyclisation of Pyrazinylhydrazones and a Route to 5H-Pyrazino [2,3-b]indole: a Synthesis of 5H-Pyrrolo [2,3-b]pyrazine and some of its Properties", J. Chem. Soc. Perkin Trans. 1, No. 13, 1976, pp. 1361-1363, XP002059634.
B.A.J. Clark et al., "Preparation of pyrrolo [2,3-b]pyrazines and pyrazino ['2,3-b]indole", Chem. Ind. (London), No. 5, 1975, pp. 215-216, SP002218234.
C.R. Hardy et al., " Ring Opening or Rearrangement versus N-Oxidation in the Action of Peracids upon Pyrrolo [2,3-b]pyridines, Pyrrolo ['2,2-b]pyrazines, and Triazolo[1,5-a]- and Triazolo[4,3-a]-pyrazine. Some Chemical and Spectroscopic Properties of the Triazolopyrazines and Their N-Oxides", J. Chem. Soc. Perkin Trans. 1, No. 2, 1980, pp. 506-511, SP002218235.

(Continued)

*Primary Examiner* — Sreeni Padmanabhan
*Assistant Examiner* — Sarah Pihonak
(74) *Attorney, Agent, or Firm* — Nixon & Vanderhye P.C.

(57) ABSTRACT

The invention relates to pyrrolo[2,3b]-pyrazine derivatives having the general Formula (I) wherein R2 and R3 are identical or different and represent H, C1-C6 alkyl, said alkyl being a straight or branched-chain alkyl, which can be substituted, R6 is an optionally substituted aromatic cycle Ar or a cycloalkyl, said cycloalkyl being optionally substituted by an aryl group which can also be substituted, R7 is H, C1-C6 alkyl, (alk.)n-hal., CH2-CH=CH2, CH2-cycloalkyl, CH2-Ar, with "alk." being a C1-C6 alkylene group, n being 1-6, Z is H or CH3. Application as active principle of pharmaceutical compositions, particularly for treating or preventing neurodegenerative disorders and proliferative disorders.

11 Claims, 5 Drawing Sheets

OTHER PUBLICATIONS

B.A.J. Clark et al., "Mass Spectrometry of Pyrrolo [2,3-b]pyrazines and Pyrazino [2,3- b]pyrazines and Pyrazino [2,3-b]indole" Org. Mass Spectrom., vol. 12, No. 7, 1977, pp. 421-423, XP002218236.

C.G. Kruse et al., "Furo-and thieno [2,3-b]pyrazines. Part 2. Chemical properties of 2-substituted derivatives" Rec. Tray. Chim. Pays-bas, vol. 97, No. 6, 1978, pp. 151-155, XP001117761.

M.L. Davis et al., "Reactions of β(Lithiomethyl)azines with Nitriles as a Route to Pyrrolopyridines, -quinolines, -pyrazines, -quinoxalines and -pyrimidines", Tetrahedron, vol. 48, No. 5, 1992, pp. 939-952, XP001118259.

C. Martin et al., "Reactions selectives de l'o.chlorobenzonitrile: SNAr", Tetrahedron Lett., vol. 30, No. 8, 1989, pp. 935-936, XP002172229.

J.-M. Vierfond et al., "Cyclisation par amination intramoleculaire dans la serie de la pyrazine", Tetrahedron Lett., vol. 22, No. 13, 1981, pp. 1219-1222, SP002172230.

* cited by examiner

DERIVATIVES OF PYRROLO-PYRAZINES HAVING A KINASE INHIBITORY ACTIVITY AND THEIR BIOLOGICAL APPLICATIONS

The invention relates to derivatives of pyrrolo-pyrazines having a kinase inhibitory activity and their biological applications. Protein kinases catalyse the phosphorylation of serine, threonine and tyrosine residues of proteins, using ATP or GTP as the phosphate donor. Protein phosphorylation is considered as one of the main post-translational mechanisms used by cells to finely tune their metabolic and regulatory pathways.

Protein kinases (an estimated 800 in the human genome), and their counterparts the protein phosphatases, appear to be involved in most human diseases. This is the reason why screening for potent and selective inhibitors of protein kinases has intensified over the last few years.

The inventors have focused their efforts on two families of kinases, cyclin-dependent kinases (CDKs) and glycogen synthase kinase-3 (GSK-3).

CDKs are involved in controlling the cell cycle apoptosis, neuronal functions and neurodegeneration, transcription and exocytosis.

GSK-3, an essential element of the WNT signaling pathway, is involved in multiple physiological processes including cell cycle regulation by controlling the levels of cyclin D1 and β-catenin, dorso-ventral patterning during development, insulin action on glycogen synthesis, axonal outgrowth, HIV-1 Tat-mediated neurotoxicity, and phosphorylation of tau, a characteristic of Alzheimer's disease. Applications of CDK/GSK-3 inhibitors are being evaluated against cancers, neurodegenerative disorders such as Alzheimer's disease, diabetes, proliferation of protozoan parasites and viral infections (HIV, cytomegalovirus and herpes virus) (1).

CDK inhibitors include the purines olomoucine, roscovitine, purvalanols, CVT-313, C2-alkylynated purines, H717 and NU2058, piperidine-substituted purines, toyocamycin, flavopiridol, indirubins, paullones, γ-butyrolactone, hymenialdisine, indenopyrazoles, the pyrimidines NU6027 and CGP60474, pyridopyrimidine, the aminopyrimidine PNU 112455A, oxindoles, PD0183812, cinnamaldehydes, quinazolines, fasclaplysin, SU9516 and benzocarbazoles (reviewed in ref. 1, 2-8). GSK-3 inhibitors include indirubins, paullones, maleimides and lithium.

The inventors have now identified a new family of kinase inhibitors selective for CDK1/2/5 and GSK-3α/β, acting in the sub-micromolar range by competing with ATP for binding to the kinase active site, as revealed by enzymological studies and crystal structure studies.

Said family has a therapeutical value in pathological situations involving CDKs and/or GSK-3α/β deregulations.

The invention thus relates to novel derivatives of pyrrolo-pyrazines.

It also relates to a method for preparing said derivatives.

According to still another aspect, the invention relates to the use of said derivatives as active principle of drugs.

The pyrrolo[2,3b]-pyrazine derivatives of the invention have the general formula (I):

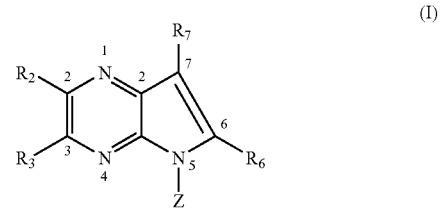

wherein:

R2 and R3 are identical or different and represent H, C1-C6 alkyl, said alkyl being a straight or branched-chain alkyl, which can be substituted, R6 is an optionally substituted aromatic cycle Ar or a cycloalkyl, said cycloalkyl being optionally substituted by an aryl group which can also be substituted, R7 is H, C1-C6 alkyl, (alk.)$_n$-hal., $CH_2$—CH=$CH_2$, $CH_2$-cycloalkyl, $CH_2$—Ar, Z is H or $CH_3$.

Preferably, R2 and R3, and/or Z and/or R7 are different from H.

Ar is preferably phenyl, naphtyl, furyl, thienyl, pyridyl, cyclopropyl phenyl, phenyl dioxolyl.

"Cycloalkyl" is a C3-C6 cycloalkyl.

Substitutions of the alkyl group, aromatic cycle or cycloalkyl are selected in the group comprising one or more halogen (F, Cl, Br, I, $CF_3$), OH, $NH_2$, N(H, alkyl); N(alkyl)$_2$, O-alkyl, COOH, COO-alkyl, $CONH_2$, CON(H,alkyl), CON(alkyl)$_2$, $NHCONH_2$, NHCON(H,alkyl), NHCON(alkyl)$_2$, N(alkyl) $CONH_2$, N(alkyl)CON(H,alkyl), N(alkyl)CON(alkyl)$_2$, alkoxy, CN, O—$SO_2$—$NH_2$, O—$SO_2$—N(H,alkyl), —O—$SO_2$—N (alkyl)$_2$, SH, S-alkyl. One or more substituents can be present.

"Alkyl" is a C1-C6 alkyl and includes isomers.

"Alkoxy" has a C1-C6 alkyl group.

"Alk." is a C1-C6 alkylene group, n is 1-6, and "hal." is F, Cl, Br, I or $CF_3$.

Said pyrrolo[2,3-b]pyrazines, also designated aloisines hereinafter, are potent kinase inhibitory scaffold, and selective for CDKs and GSK-3α/β, acting for most of them in the sub-micromolar range.

Kinetic studies, as well as the resolution of co-crystal structures of CDK/aloisines demonstrate that aloisines act by competitive inhibition of ATP binding to the catalytic subunit of the kinase. They interact with the ATP-binding pocket through two hydrogen bonds with backbone nitrogen and oxygen atoms of Leu 83.

Said aloisines are also characterized in that they inhibit cell proliferation by arresting cells both in G1 and G2 as illustrated by the Examples hereinafter.

Preferred derivatives of pyrrolo-pyrazines have formula (II):

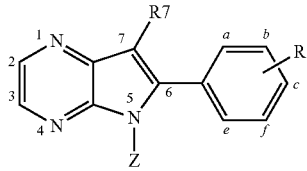

wherein:
the phenyl group at position 6 is substituted by one, two or three R substituents selected in the group comprising:
H, —OH, alkyl, —O alkyl, hal., —$NH_2$, —N(H,alkyl), —N(alkyl)$_2$, —O—$SO_2$—$NH_2$, —O—$SO_2$—N(H, alkyl), —O—$SO_2$—N(alkyl)$_2$, —COOH, —COO-alkyl, $CONH_2$, —CON(H,alkyl), —CON(alkyl)$_2$,
R7 is H, alkyl, (alk.)$_n$ hal., —$CH_2$—CH=$CH_2$, (alk.)$_n$-cycloalkyl, alk.-Ar, and
Z is H or $CH_3$.
In a preferred group, Z and/or R7 are different from H.

A preferred group of said family has an $IC_{50}$ value ≦10 μM with respect to correspond to CDK1/cyclin B, CDK5/p25 and GSK-3. They correspond to the derivatives of formula (II) wherein
R=H, OH, alkoxy, hal., alkyl and R7=H or to derivatives wherein R=alkoxy, and R7=alkyl, (alk.)$_n$-hal., $CH_2$—CH=$CH_2$, or
R=O—$SO_2$—N-(alkyl)$_2$ preferred, hal., OH, R7=alkyl, n=1-3 and Z=H.

A more preferred group of said family of formula (II) has an $IC_{50}$ value ≦5 μM with respect to CDK1/cyclin B, CDK5/p25 and GSK-3.

They correspond to the derivatives of formula (II) wherein R=H, p-alkoxy, p- and m-alkoxy, p-OH, p-hal., p-alkyl, p-O—$SO_2$—N(alkyl)$_2$, R7 is alkyl, (alk.)$_n$-hal., $CH_2$—CH=$CH_2$, or H, Z is H, and n=1-3.

Preferred derivatives of said group correspond to compounds wherein (a-e correspond to the position of R on the phenyl group):
the phenyl group is unsubstituted and R7 is H, or
Ra, Rb and Rd=H, Rc=alkoxy, OH or hal., and R7=H, or
Ra, Rb and Rd=H, Rc=alkoxy and R7=alkyl, or
Ra and Rd=H, Rb and Rc=alkoxy and R7=alkyl, or
Ra, Rb and Rd=H, Rc=alkoxy and R7 alkyl, or
Ra, Rb and Rd=H, Rc=alkoxy, OH, hal. and R7=alkyl, (alk.)$_n$-hal, $CH_2$—CH=$CH_2$, or
Ra, Rb and Rd=H, Rc=OH, R7=alkyl.

A still more preferred group of said family of formula (II) has an $IC_{50}$≦1 μM with respect to CDK1/cyclin B, CDK5/p25 and GSK-3.

They correspond to derivatives of formula (II) wherein R is p-alkoxy, p-0-$SO_2$—N-(alkyl)$_2$, p-OH and R7 is alkyl.

Preferred derivatives correspond to compounds with Ra, Rb and Rd=H, Rc=alkoxy, O—$SO_2$—N(alkyl)$_2$, or OH and R7=alkyl.

In a particularly more preferred group, the derivatives have an $IC_{50}$≦0.5 μM with respect to CDK1/cyclin B, CDK5/p25 and GSK-3. Particularly advantageous derivatives have Ra, Rb and Rd=H, Rc=alkoxy or OH and R7=alkyl.

Another preferred group of said family of formula (II) has an $IC_{50}$ value ≦10 μM with respect to CDK1/cyclin B and CDK5/p25 or GSK-3, or to CDK5/p25 and GSK-3.

The invention particularly relates to the group with derivatives having an $IC_{50}$≦10 μM with respect to CDK5/p25 and GSK-3.

In such a group, R=H, OH, alkoxy, hal., alkyl, O—$SO_2$—N(alkyl)$_2$, and R7=H, alkyl, (alk.)$_n$-hal., $CH_2$—CH=$CH_2$.

Preferred derivatives of said group have an $IC_{50}$ value ≦5 μM with respect to CDK5/p25 and GSK-3. In said derivatives R is H, p-alkoxy, OH, hal., O—$SO_2$—N-(alkyl)$_2$ and R7 is H, alkyl, (alk.)$_n$, hal., $CH_2$—CH=$CH_2$.

Advantageous derivatives have Ra, Rb, Rc, Rd and R7=H, or Ra, Rb and Rd=H, Rc=alkoxy, hal., (alk.)$_n$-hal., or OH and R7=H, or Ra, Rb and Rd=H, Rc=alkoxy or $OSO_2$—N(alkyl)$_2$, hal., OH and R7=alkyl, or Ra and Rd=H, Rb and Rc=alkoxy and R7=alkyl.

More preferred derivatives of said group have an $IC_{50}$ value ≦1 μM with respect to CDK5/p25 and GSK-3. In such derivatives,
R=p-alkoxy, p- and m-dialkoxy, hal., p-O—$SO_2$—N(alkyl)$_2$, p-OH and R7=H or alkyl.

Particularly advantageous derivatives have Ra, Rb, Rd H, Rc=alkoxy and R7=alkyl, or Ra and Rd=H, Rb and Rc=alkoxy and R7=alkyl, or Ra, Rb and Rd=H, Rc=O—$SO_2$—N(alkyl)$_2$ or OH and R7=alkyl.

Still more preferred derivatives have an $IC_{50}$≦0.5 μM with respect to CDK5/p25 and GSK-3. Advantageous derivatives have Ra, Rb, and Rd=H, Rc=alkoxy or OH, and R7=alkyl.

In another group of the invention, the derivatives have an $IC_{50}$≦10 μM with respect to CDK1 and GSK3.

In derivatives of said group R=H, OH, alkoxy, hal., alkyl, CN, O—$SO_2$—N(alkyl)$_2$ and R7=H, alkyl, (alk.)$_n$-hal, $CH_2$—CH=$CH_2$, alk.-cycloalkyl, alk.-aryl.

In a preferred group of said family, the derivatives have an $IC_{50}$≦5 μM with respect to CDK1 and GSK-3.

In advantageous derivatives, R=H, p-alkoxy, p- and m-alkoxy, p-OH, p-hal., p-O—$SO_2$—N(alkyl)$_2$, p-CN, and R7=H or alkyl, (alk.)$_n$ hal., $CH_2$—CH=$CH_2$, (alk.)$_n$-cycloalkyl, (alk.)$_n$-aryl.

Corresponding preferred derivatives have Ra, Rb and Rd=H,
Rc=alkoxy, OH, hal., alkyl, CN and R7=H, or Ra, Rb, Rd=H,
Rc=alkoxy and R7=alkyl, (alk.)$_n$-hal. or $CH_2$—CH=$CH_2$, or Ra and Rd=H, Rb and Rc=alkoxy and R7=alkyl, or Ra, Rb and Rc=H, Rd=O—$SO_2$—N-(alkyl)$_2$, and R7=alkyl, or Ra, Rb and Rd=H, Rc=hal. and R7=(alk.)$_n$-aryl.

In a still more preferred group of said family, the derivatives have an $IC_{50}$ value ≦1 μM with respect to CDK1 and GSK-3.

Corresponding derivatives have R=p-alkoxy, p-O—$SO_2$—N(alkyl)$_2$, p-hal., H, p-OH, R7=alkyl, or (alk.)$_n$-hal, $CH_2$—CH $CH_2$, (alk.)$_n$-cycloalkyl, (alk.)$_n$-aryl.

Preferred derivatives have Ra, Rb and Rd=H, Rc=alkoxy, OH, O—$SO_2$—N(alkyl)$_2$, hal. and R7=alkyl, $CH_2$—CH=$CH_2$, $CH_2$-cycloalkyl.

In a particularly more preferred group of said family, the derivatives have an $IC_{50}$ value ≦0.5 μM with respect to CDK1/cyclin B and GSK-3.

Advantageous derivatives have Ra, Rb and Rd=H, Rc alkoxy or OH and R7=alkyl.

The invention also relates to the group with derivatives having an $IC_{50}$≦10 μM with respect to CDK1/cyclin B and CDK5/p25.

In such a group, R=H, OH, alkoxy, hal., alkyl, O—$SO_2$—N(alkyl)$_2$ and R7=H, alkyl, (alk.)$_n$-hal., $CH_2$—CH=$CH_2$.

Preferred derivatives have an $IC_{50}$≦5 μM with respect to CDK1/cyclin B and GSK-3.

In such derivatives, R is preferably H, O-alkoxy, p-alkoxy, m- and p-alkoxy, p-OH., p-hal., p-O—SO$_2$—N(alkyl)$_2$ and R7 is H, alkyl, (alk.)$_n$-hal., CH$_2$—CH═CH$_2$.

Particularly advantageous derivatives have Ra, Rb, Rc, Rd and R7═H, or Ra═OH and Rb, Rc, Rd and R7═H, or Rc, Rb and Rd═H, Rc═alkoxy, OH or hal. and R7═H, (alk.)$_n$-hal., CH$_2$—CH═CH$_2$, alkyl, or Ra and Rd═H, Rb and Rc═alkoxy and R7═H, or Ra, Rb and Rd═H, Rc═O—SO$_2$—N-(alkyl)$_2$ or hal. and R7═alkyl.

In a still more preferred group, the derivatives have an IC$_{50}$≦1 μM with respect to CDK1/cyclin B and GSK-3.

Advantageous derivatives have R═p-alkoxy, p-O—SO$_2$—N(alkyl)$_2$, p-hal., p-OH and R7═alkyl.

Particularly preferred derivatives have Ra, Rb and Rd═H, Rc═alkoxy OH or O—SO$_2$—N(alkyl)$_2$ and R7═alkyl.

In a particularly preferred group the derivatives have an IC$_{50}$≦0.5 μM with respect to CDK1/cyclin B and GSK-3.

In preferred derivatives, Ra, Rb, and Rd═H, Rc═alkoxy or OH and R7═alkyl.

Another preferred family with an IC$_{50}$≦10 μM with respect to CDK1/cyclin B, CDK5 and GSK-3 has formula (III), and even ≦5 μM with respect to CDK5/p25 and GSK-3.

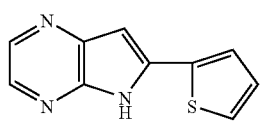

(III)

Still another preferred family has formula IV with an IC$_{50}$≦5 μM with respect to CDK1/cyclin B, CDK5/p25 and GSK-3.

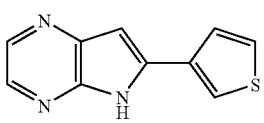

(IV)

Said derivatives have interestingly an IC$_{50}$ value ≦1 μM with respect to CDK5/p25 and GSK-3.

The invention also relates to a method for preparing said aloisines comprising reacting alkyl-pyrazines of formula (V):

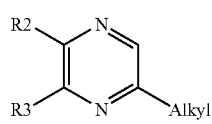

(V)

wherein:
R1 and R3 are as above defined, and Alkyl is a C1-C6 alkyl, with aromatic nitriles, R6CN, wherein R6 is as above defined.

Advantageously, the alkylpyrazine derivatives of formula (V) are added to an organic solvent containing butyllithium or analog, at a temperature not exceeding 0° C. and preferably of about −40° C. The resulting solution is stirred during 30 min to about 1 h. The nitrile derivative is then added and the solution is stirred during 30 min to about 1 h, and further at the ambient (around 20° C.) for about 1 to 20 h.

After hydrolysis, the resulting derivative is recovered, purified and crystallized if desired.

Alkylpyrazines can be obtained by reaction of pyrazinyl-methyllithium with bromoalcanes, and benzonitriles. Demethylation of methoxy compounds can be achieved by refluxing in, acidic conditions. The time required for demethylation varied from 3-20 h.

As above mentioned, and as illustrated in the Examples hereinafter, said compounds strongly inhibit CDK1 and/or CDK5 and/or GSK-3.

By acting on said kinases, which represent the major kinases involved in the hyperphosphorylation of substrates in neurodegenerative diseases, said derivatives are of great interest as active principles of drugs for preventing and treating corresponding conditions. They have also anti proliferative effects.

The invention thus relates to pharmaceutical compositions comprising an effective amount of at least one derivative as above defined as active principle in association with a pharmaceutically acceptable carrier.

Said carrier may be solid, or liquid, depending on the administration form.

Said pharmaceutical compositions are useful for treating or preventing, neurodegenerative disorders such as Alzheimer's disease or Parkinson's diseases. They are also useful for treating invention also relates to the use of said pharmaceutical compositions for treating proliferative disorders such as cancers, or the proliferation of unicellular or pluricellular parasites. Other applications comprise the use of said pharmaceutical compositions against cardiovascular disorders linked to proliferation. They also comprise their use for treating viral injections (HIV, cytomegalovirus and herpes virus. The invention also relates to the use of said derivatives as herbicides.

Said pharmaceutical compositions can be administered in various forms e.g. orally, topically, by injection (intravenously, subcutaneously, intraperitoneally, or rectally). They are more particularly administered by the oral route.

For administration by the oral route, lozenges, compressed tablets, pills, tablets, capsules, drops, syrups, suspensions or emulsions, may be used. These compositions advantageously comprise 100 to 1000 mg of active principle per dose unit, preferably 300 to 600 mg.

Other forms of administration include injectable solutions for the intravenous, subcutaneous or intramuscular route, formulated from sterile or sterilizable solutions. They can also be suspensions or emulsions.

These injectable forms comprise 100 to 1000 mg of active principle preferably 300 to 600 mg, per dose unit.

By way of indication, the dosage which can be used in a patient in need thereof corresponds to the following doses for example, 100 to 1000 mg/day are thus administered to the patient 1 to 4 times per day for the treatment of neurodegenerative disorders.

The invention also relates to biological reagents, the active principles of which consist of the compounds of formula (I) as above-defined.

These reagents can be used as references or standards in studies of cell division and phosphorylation mechanisms.

Other characteristics and advantages of the invention are given in the Examples disclosed hereinafter, with reference to FIGS. 1 to 7 which represent, respectively;

A/ CHEMISTRY

Figure 1:
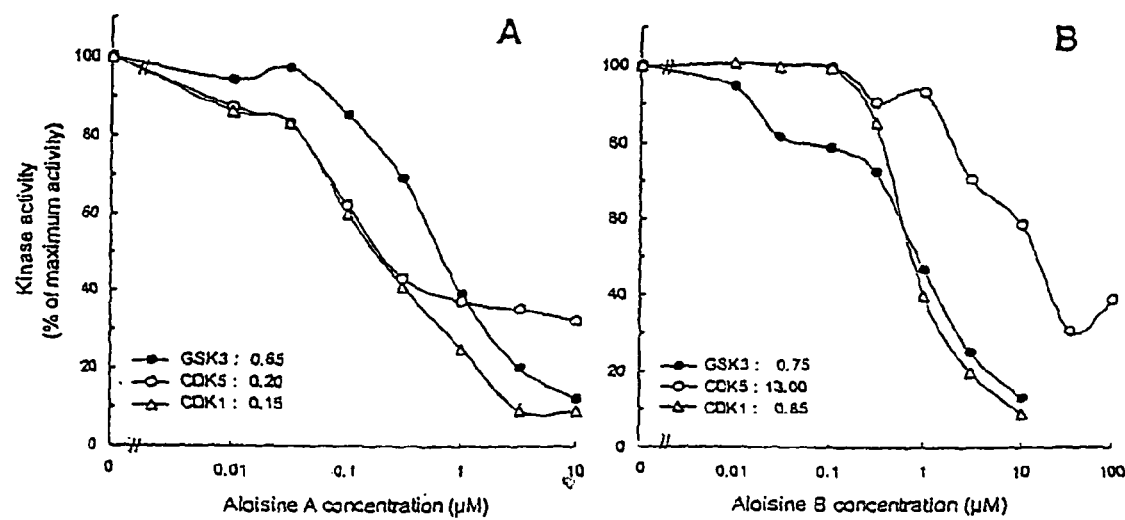
FIG. 1: CDK1/cyclin B, CDK5/p25 and GSK-3β inhibition results with aloisines of the invention, FIGS. 2A to 2C, enzyme activities for aloisine A in the presence of ATP (CD1/cyclin B.

Melting points were measured in open capillary tubes on an Electrothermal 9200 apparatus and are uncorrected. IR spectra were taken in KBr on an ATI Mattson genesis series FTIR. $^1$H NMR were recorded on a Varian EM 360 A spectrometer (60 MHz) and chemical shifts (ppm) are reported relative to TMS. Signals are designated as follows: bs (broad singlet), s (singlet), d (doublet), dd (doublet of doublets), t (triplet), m (multiplet). Mass spectra were determined on a LKB 209 (EI at 70 eV). Elemental microanalyses are indicated by the symbol of the elements and the results were within ±0.4% of the theoretical values unless otherwise stated; they were performed on a Perkin Elmer 240 apparatus.

All experiments involving butyllithium or sodium hydride were carried out in dried apparatus under an atmosphere of dry oxygen-free nitrogen. Tetrahydrofuran (THF) was distilled from benzophenone-sodium. Diisopropylamine and methyl-heterocycles were distilled and stored over baryum oxide. Butyllithium (1.6M solution in hexane) was supplied by Acros and was assayed by titration against diphenylacetic acid. Alkyl and aralkylpyrazines were prepared according to usual procedures. Grace silicagel 60 A 20-45 μm was employed for column chromatographies. 2-Phenylindole was purchased from Aldrich and used as received.

a—General Method for the Synthesis of Aloisines

Diisopropylamine (2.23 g; 0.022 mol) in THF (50 mL) was cooled to 0° C., and butyllithium (0.022 mol) was added dropwise. After stirring 30 min at 0° C., the solution was cooled to −40° C. before, addition of the alkylpyrazine derivative (0.02 mol) in THF (20 mL). After 30 min, the nitrile derivative R6-CN (0.001 mol) in THF (20 mL) was added, and the solution was stirred for 30 min at −40° C. and further (1 h-20 h) at 20° C., then hydrolyzed with a 10% aqueous solution of NH$_4$Cl. The organic layer was dried over Na$_2$SO$_4$, and concentrated under vacuum. The crude product was chromatographied on silicagel, eluted with methylene chloride, then ethyl acetate. If necessary the product was crystallized from ethanol or methylene chloride-ethanol mixture.

b—Experimental Results 6-(2-Furyl)[5H]pyrrolo[2,3-b]pyrazine (1, RP19): mp 232.6° C.; IR 3157, 3143, 3102 cm$^{-1}$; $^1$H NMR δ (60 MHz, DMSO-d$_6$) 6.50-6.70 (m, 1H), 6.80 (s, 1H), 7.05 (d, 1H, J=3 Hz), 7.80 (bs, 1H), 8.20 and 8.35 (2d, 1H each, J=3 Hz), 12.45 (bs, 1H). Anal. (C$_{10}$H$_7$N$_3$O) C, H, N.

6-(2-Thienyl)[5H]pyrrolo[2,3-b]pyrazine (2, RP6): mp 260.3° C.; IR 3208, 3150, 3068 cm$^{-1}$; $^1$H NMR δ (60 MHz, DMSO-d$_6$) 6.95 (bs, 1H), 7.15-7.45 (m, 1H), 7.75 (s, 1H), 7.85 (bd, 1H), 8.25 and 8.45 (2d, 1H each, J=2.8 Hz), 12.85 (bs, 1H). Anal. (C$_{10}$H$_7$N$_3$S) C, H, N.

6-(3-Thienyl) [5H]]pyrrolo[2,3-b]pyrazine (3, RP128): mp 230° C. dec; IR 3095, 3050, 3000 cm$^{-1}$; $^1$H NMR δ (60 MHz, DMSO-d$_6$) 6.95 (s, 1H), 7.60-7.75 (m, 2H), 8.10-8.20 (m, 2H), 8.30 (d, 1H, J=2.6 Hz), 12.30 (bs, 1H). Anal. (C$_{10}$H$_7$N$_3$S) C, H, N.

6-(2-Pyridyl)[5H]pyrrolo[2,3-b]pyrazine (4, RP13): mp 233.1° C.; IR 3100, 3059 cm$^{-1}$; $^1$H NMR δ (60 MHz, DMSO-d$_6$) 7.30-7.60 (m, 2H), 7.95-8.20 (m, 2H), 8.30 and 8.45 (2d, 1H each, J=2.8 Hz), 8.75 (d, 1H, J=5 Hz), 12.65 (bs, 1H). Anal. (C$_{11}$H$_8$N$_4$) C, H, N.

6-Phenyl[5H]pyrrolo[2,3-b]pyrazine (5, RP7): mp 216° C. (lit mp 215-216° C.); IR 3135, 3050 cm$^{-1}$; $^1$H NMR δ (60 MHz, DMSO-d$_6$) 7.00 (s, 1H), 7.55 (m, 3H), 7.90 (m, 2H), 8.25 and 8.50 (2d, 1H each, J=3 Hz), 11.90 (bs, 1H); MS m/e 209 (M$^+$) (100). Anal. (C$_{12}$H$_9$N$_3$) C, H, N.

6-(1-Naphtyl) [5H]pyrrolo[2,3-b]pyrazine (6, RP17): mp 216.4° C.; IR 3214, 3110, 3048 cm$^{-1}$; $^1$H NMR δ (60 MHz, DMSO-d$_6$) 6.95 (s, 1H), 7.50-7.85 (m, 4H), 7.95-8.40 (m, 4H), 8.50 (d, 1H, J=2.5 Hz), 12.05 (bs, 1H). Anal. (C$_{16}$H$_{11}$N$_3$) C, H, N.

3-Methyl-6-phenyl[5H]pyrrolo[2,3-b]pyrazine (8, RP18): mp 261.8° C.; IR 3104, 3030, 2985, 2915, 2878, 2801 cm$^{-1}$; $^1$H NMR δ (60 MHz, DMSO-d$_6$) 2.55 (s, 3H), 7.15 (s, 1H), 7.35-7.60 (m, 3H), 7.75-8.10 (m, 2H), 8.40 (s, 1H), 12.30 (bs, 1H); MS m/e 209 (M$^+$) (100). Anal. (C$_{13}$H$_{11}$N$_3$) C, H, N.

6-[1-(4-Chlorophenyl)-1-cyclopropyl][5H]pyrrolo[2,3-b]pyrazine (9, RP124): mp 189.7° C.; IR 3210, 3125, 3049, 3000, 2940, 2850 cm$^{-1}$; $^1$H NMR δ (60 MHz, DMSO-d$_6$) 1.50 (d, 4H), 6.15 (s, 1H), 7.30 (s, 4H), 8.10 and 8.25 (2d, 1H each, J=3 Hz), 12.00 (bs, 1H). Anal. (C$_{15}$H$_{12}$N$_3$Cl) C, H, N.

6-(2-Methoxyphenyl)[5H]pyrrolo[2,3-b]pyrazine (10, RP9): mp 156.9° C.; IR 3080, 3051, 2925, 2887, 2830 cm$^{-1}$; $^1$H NMR δ (60 MHz, DMSO-d$_6$) 3.90 (s, 3H), 6.95-7.35 (m, 4H), 7.80-8.10 (m, 1H), 8.20 and 8.35 (2d, 1H each, J=2.5 Hz), 11.90 (bs, 1H). Anal. (C$_{13}$H$_{11}$N$_3$O) C, H, N.

6-(3-Methoxyphenyl)[5H]pyrrolo[2,3-b]pyrazine (12, RP10): mp 195.7° C.; IR 3123, 2968, 2921, 2836 cm$^{-1}$; $^1$H NMR δ (60 MHz, DMSO-d$_6$) 3.95 (s, 3H), 6.90-7.80 (m, 5H), 8.25 and 8.40 (2d, 1H each, J=2.5 Hz), 12.55 (bs, 1H). Anal. (C$_{13}$H$_{11}$N$_3$O) C, H, N.

6-(4-Methoxyphenyl)[5H]pyrrolo[2,3-b]pyrazine (14, RP11): mp 256.1° C. (lit. 238-240° C. dec.); IR 3143, 3035, 2959, 2857 cm$^{-1}$; $^1$H NMR δ (60 MHz, DMSO-d$_6$) 3.80 (s, 3H), 6.95-7.10 (m, 3H), 8.00 (d, 2H, J=8 Hz), 8.15 and 8.35 (2d, 1H each, J=2.6 Hz), 12.35 (bs, 1H). Anal. (C$_{13}$H$_{11}$N$_3$O) C, H, N.

6-(3,5-Dimethoxyphenyl)[5H]pyrrolo[2,3-b]pyrazine (16, RP21): mp 216.7° C.; IR 3150, 2950, 2880 cm$^{-1}$; $^1$H NMR δ (60 MHz, DMSO-d$_6$) 3.90 (s, 6H), 6.55 (s, 1H), 7.20 (m, 3H), 8.15 and 8.35 (2d, 1H each, J=2.5 Hz), 12.40 (bs, 1H). Anal. (C$_{14}$H$_{13}$N$_3$O$_2$) C, H, N.

6-(3,4,5-Trimethoxyphenyl)[5H]pyrrolo[2,3-b]pyrazine (17, RP16): mp 231.7° C.; IR 3098, 2964, 2939, 2834 cm$^{-1}$; $^1$H NMR δ (60 MHz, DMSO-d$_6$) 3.75 (s, 3H), 3.95 (s, 6H), 7.25 (s, 1H), 7.40 (bs, 2H), 8.25 and 8.40 (2d, 1H each, J=2 Hz), 12.45 (bs, 1H). Anal. (C$_{15}$H$_{15}$N$_3$O$_3$) C, H, N.

6-(4-Fluorophenyl)[5H]pyrrolo[2,3-b]pyrazine (18, RP76): mp 244° C. dec; IR 3149 cm$^{-3}$; $^1$H NMR δ (60 MHz, DMSO-d$_6$) 7.05-7.50 (m, 3H), 7.65-8.10 (m, 2H), 8.20 and 8.35 (2d, 1H each, J=2.4 Hz), 12.45 (bs, 1H). Anal. (C$_{12}$H$_8$N$_3$F) C, H, N.

6-(4-Chlorophenyl)[5H]pyrrolo[2,3-b]pyrazine (19, RP14): mp 250° C. dec (lit. 250° C. dec.); IR 3300 cm$^{-1}$; $^1$H NMR δ (60 MHz, DMSO-d$_6$) 7.20 (s, 1H), 7.55 and 8.05 (2d, 2H each, J=8. Hz), 8.20 and 8.35 (2d, 1H each, J=2.4 Hz), 12.45 (bs, 1H). Anal. (C$_{12}$H$_8$N$_3$Cl) C, H, N.

6-(3,5-Dichlorophenyl)[5H]pyrrolo[2,3-b]pyrazine (20, RP15): mp 252° C. dec; IR 3216, 3164, 3114 cm$^{-1}$; $^1$H NMR δ (60 MHz, DMSO-d$_6$) 7.35 (s, 1H), 7.75 (m, 1H), 8.15 (d, 2H), 8.25 and 8.40 (2d, 1H each, J=2.2 Hz), 12.40 (bs, 1H). Anal. (C$_{12}$H$_7$N$_3$Cl$_2$) C, H, N.

6-(4-Bromophenyl) [5H]pyrrolo[2,3-b]pyrazine (21, RP77): mp 256° C. dec; IR 3211, 3109 cm$^{-1}$; $^1$H NMR δ (60 MHz, DMSO-d$_6$) 7.20 (s, 1H), 7.70 and 8.00 (2d, 2H each, J=8.2 Hz), 8.20 and 8.35 (2d, 1H each, J=2.5 Hz), 12.45 (bs, 1H). Anal. (C$_{12}$H$_8$N$_3$Br) C, H, N.

6-(4-Trifluoromethylphenyl)[5H]pyrrolo[2,3-b]pyrazine (22, RP8): mp 238° C. dec; IR 3164 cm$^{-1}$; $^1$H NMR δ (60 MHz, DMSO-d$_6$) 7.35 (s, 1H), 7.85 (d, 2H, J=8.2 Hz), 8.10-8.50 (m, 4H), 12.70 (bs, 1H). Anal. (C$_{13}$H$_8$N$_3$F$_3$) C, H, N.

6-(4-Cyanophenyl) [5H]pyrrolo[2,3-b]pyrazine (23, RP20): mp 340° C. dec; IR 3464, 3056, 2205 cm$^{-1}$; $^1$H NMR δ (60 MHz, DMSO-d$_6$) 7.45 (s, 1H), 7.90-8.65 (m, 6H), 12.85 (bs, 1H). Anal. (C$_{13}$H$_8$N$_4$) C, H, N.

6-(4-Methylphenyl)[5H]pyrrolo[2,3-b]pyrazine (24, RP78): mp 265.4° C.; IR 3150, 3120, 2940, 2920 cm$^{-1}$; $^1$H NMR δ (60 MHz, DMSO-d$_6$) 2.40 (s, 3H), 7.05 (s, 1H), 7.30 and 7.90 (2d, 2H each, J=8 Hz), 8.15 and 8.30 (2d, 1H each, J=2.4 Hz), 12.45 (bs, 1H). Anal. (C$_{13}$H$_{11}$N$_3$) C, H, N.

6-[4-(2-Dioxolyl)-phenyl][5H]pyrrolo[2,3-b]pyrazine (25, RP122): mp 265.6° C.; IR 3120, 2980, 2889 cm$^{-1}$; $^1$H NMR δ (60 MHz, DMSO-d$_6$) 3.95 (s, 4H), 5.75 (s, 1H), 7.15 (s, 1H), 7.50 and 8.05, (2d, 2H each, J=7 Hz), 8.20 and 8.35 (2d, 1H each, J=3 Hz), 12.45 (bs, 1H). Anal. (C$_{15}$H$_{13}$N$_3$O$_2$) C, H, N.

6-(4-Dimethylaminophenyl)[5H]pyrrolo[2,3-b]pyrazine (26, RP129): mp 271° C. dec; IR 3211, 3157, 2900, 2818, cm$^{-1}$; $^1$H NMR δ (60 MHz, DMSO-d$_6$) 3.15 (s, 6H), 6.80-6.90 (m, 3H), 7.85 (d, 2H, J=8.Hz), 8.05 and 8.20 (2d, 1H each, J=3 Hz), 12.15 (bs, 1H). Anal. (C$_{14}$H$_{14}$N$_4$) C, H, N.

6-(4-Methoxyphenyl)-7-methyl[5H]pyrrolo[2,3-b]pyrazine (27, RP95): mp 221.6° C.; IR 3142, 3043, 2955, 2844 cm$^{-1}$; $^1$H NMR δ (60 MHz, DMSO-d$_6$) 2.40 (s, 3H), 3.80 (s, 3H), 7.10 and 7.70 (2d, 2H each, J=7 Hz), 8.15 and 8.30 (2d, 1H each, J=2.6 Hz), 12.00 (bs, 1H). Anal. (C$_{14}$H$_{13}$N$_3$O) C, H, N.

6-(3,4-Methoxyphenyl)-7-methyl[5H]pyrrolo[2,3-b]pyrazine (29, RP123): mp 230.2° C.; IR 3102, 2963, 2920, 2850 cm$^{-1}$; $^1$H NMR δ (60 MHz, DMSO-d$_6$) 2.55 (s, 3H), 3.80 (s, 3H), 3.85 (s, 3H), 7.00-7.40 (m, 3H), 8.15 and 8.30 (2d, 1H each, J=3 Hz), 12 (bs, 1H). Anal. (C$_{15}$H$_{15}$N$_3$O$_2$) C, H, N.

6-(4-Chlorophenyl)-7-methyl[5H]pyrrolo[2,3-b]pyrazine (30, RP80): mp 260° C. dec.; IR 3148, 2920, 2853 cm$^{-1}$; $^1$H NMR δ (60 MHz, DMSO-d$_6$) 2.40 (s, 3H), 7.40-7.85 (m, 4H), 8.15 and 8.30 (2d, 1H each, J=2.5 Hz), 12.00 (bs, 1H). Anal. (C$_{13}$H$_{10}$N$_3$Cl) C, H, N.

6-(4-Dimethylaminosulfamoyloxyphenyl)-7-methyl[5H]pyrrolo[2,3-b]pyrazine (31, RP125): mp 235.1° C.; IR 3140, 3045, 2970, 2925, 2880 cm$^{-1}$; $^1$H NMR δ (60 MHz, DMSO-d$_6$) 2.45 (s, 3H), 2.95 (s, 6H), 7.45 and 7.90 (2d, 2H each, J=8 Hz), 8.30-8.50 (m, 2H), 12.25 (bs, 1H). Anal. (C$_{15}$H$_{16}$N$_4$SO$_3$) C, H, N.

6-(4-Methoxyphenyl)-7-propyl[5H])pyrrolo[2,3-b]pyrazine (32, RP127): mp 188.5° C.; IR 3215, 3158, 3055, 2958, 2934, 2866, 2836 cm$^{-1}$; $^1$H NMR δ (60 MHz, DMSO-d$_6$) 0.9 (t, 3H, J=7 Hz), 1.70 (m, 2H), 2.80 (t, 2H, J=7 Hz), 3.80 (s, 3H), 7.05 and 7.65 (2d, 2H each, J=8 Hz), 8.15 and 8.30 (2d, 1H each, J=3 Hz), 12.00 (bs, 1H). Anal. (C$_{16}$H$_{17}$N$_3$O) C, H, N.

7-Allyl-6-(4-methoxyphenyl)[5H]pyrrolo[2,3-b]pyrazine (34, RP110): mp 193.8° C.; IR 3135, 3063, 2962, 2934, 2878, 2838 cm$^{-1}$; $^1$H NMR δ (60 MHz, CDCl$_3$) 3.65-3.85 (m, 2H), 3.90 (s, 3H), 4.80-5.20 (m, 2H), 5.75-6.45 (m, 1H), 7.10 and 7.75 (2d, 2H each, J=8.2 Hz), 8.05 and 8.40 (2d, 1H each, J=2.4 Hz), 11.85 (bs, 1H). Anal. (C$_{16}$H$_{15}$N$_3$O) C, H, N.

7-(3-Chloropropyl)-6-(4-methoxyphenyl)[5H]pyrrolo[2,3-b]pyrazine (35, RP126): mp 178° C. dec; IR 3220, 3159, 3050, 3000, 2835 cm$^{-1}$; $^1$H NMR δ (60 MHz, DMSO-d$_6$) 2.00-2.60 (m, 2H), 3.00 (m, 2H), 3.60 (t, 2H, J=6 Hz), 3.80 (s, 3H), 7.10 and 7.70 (2d, 2H each, J=8 Hz). 8.15 and 8.35 (2d, 1H each, J=3 Hz), 12.00 (bs, 1H). Anal. (C$_{16}$H$_{16}$N$_3$OCl) C, H, N.

7-Isopropyl-6-(4-methoxyphenyl)[5H]pyrrolo[2,3-b]pyrazine (36, RP102): mp 204.8° C.; IR 3135, 3050, 2957, 2924, 2859 cm$^{-1}$; $^1$H NMR δ (60 MHz, DMSO-d$_6$) 1.30 (d, 6H), 3.50 (m, 1H), 3.80 (s, 3H), 7.10 and 7.55 (2d, 2H each, J=8 Hz), 8.15 and 8.35 (2d, 1H each, J=2.4 Hz), 11.75 (bs, 1H). Anal. (C$_{16}$H$_{17}$N$_3$O) C, H, N.

6-(4-Chlorophenyl)-7-isopropyl[5H]pyrrolo[2,3-b]pyrazine (37, RP90): mp 208.6° C.; IR 3130, 3051, 2977, 2925, 2869 cm$^{-1}$; $^1$H NMR δ (60 MHz, CDCl$_3$) 1.50 (d, 6H, J=6 Hz), 3.25 (m, 1H), 7.60 (s, 4H), 8.20 and 8.35 (2d, 1H each, J=2.5 Hz), 12.00 (bs, 1H). Anal. (C$_{15}$H$_{14}$N$_3$Cl) C, H, N.

7-n-Butyl-6-(4-methoxyphenyl)[5H]pyrrolo[2,3-b]pyrazine (38, RP106): mp 183.8° C.; IR 3143, 3050, 2956, 2934, 2870 cm$^{-1}$; $^1$H NMR δ (60 MHz, DMSO-d$_6$) 1.00 (t, 3H, J=7.2 Hz), 1.60 (m, 4H), 3.00 (t, 2H, J=7.6 Hz), 3.90 (s, 3H), 7.10 and 7.70 (2d, 2H each, J=8 Hz), 8.00 and 8.30 (2d, 1H each, J=2.6 Hz), 11.75 (bs, 1H). Anal. (C$_{17}$H$_{19}$N$_3$O) C, H, N.

7-n-Butyl-6-(4-chlorophenyl)[5H]pyrrolo[2,3-b]pyrazine (40, RP108): mp 200° C.; IR 3161, 3048, 2954, 2924, 2856 cm$^{-1}$; $^1$H NMR δ (60 MHz, DMSO-d$_6$) 0.90 (t, 3H, J=6 Hz), 1.20-2.00 (m, 4H), 2.95 (t, 2H, J=7.2 Hz), 7.65 (s, 4H), 8.25 and 8.40 (2d, 1H each, J=2.5 Hz), 12.05 (bs, 1H). Anal. (C$_{16}$H$_{16}$N$_3$Cl) C, H, N.

7-n-Heptyl-6-(4-methoxyphenyl)[5H]pyrrolo[2,3-b]pyrazine (41, RP111): mp 132.5° C.; IR 3142, 3064, 2955, 2925, 2850 cm$^{-1}$; $^1$H NMR δ (60 MHz, CDCl$_3$) 0.90-2.00 (m, 13H), 3.05 (t, 2H, J=7.2 Hz), 3.90 (s, 3H), 7.05 and 7.70 (2d, 2H each, J=8.2 Hz), 8.00 and 8.40 (2d, 1H each, J=3 Hz), 12.05 (bs, 1H). Anal. (C$_{20}$H$_{25}$N$_3$O) C, H, N.

6-(4-Methoxyphenyl)-7-methylcyclopropyl[5H]pyrrolo[2,3-b]pyrazine (42, RP104): mp 193.9° C.; IR 3142, 3080, 3046, 3000, 2931, 2820 cm$^{-1}$; $^1$H NMR δ (60 MHz, DMSO-d$_6$) 0.20-0.50 (m, 4H), 1.00-1.40 (m, 1H), 2.90 (d, 2H, J=6 Hz), 3.85 (s, 3H), 7.15 and 7.75 (2d, 2H each, J=8.2 Hz), 8.20 and 8.40 (2d, 1H each, J=2.6 Hz), 12.20 (bs, 1H). Anal. (C$_{17}$H$_{17}$N$_3$O) C, H, N.

7-Benzyl-6-phenyl[5H]pyrrolo[2,3-b]pyrazine (44, RP92): mp 209.8° C.; IR 3144, 3056, 3024, 2929, 2871 cm$^{-1}$; $^1$H NMR δ (60 MHz, DMSO-d$_6$) 4.30 (s, 2H), 7.20 (s, 6H), 7.75-8.25 (m, 4H), 8.30 and 8.40 (2d, 1H each, J=3 Hz), 12.25 (bs, 1H). Anal. (C$_{19}$H$_{15}$N$_3$) C, H, N.

7-Benzyl-6-(4-chlorophenyl)[5H]pyrrolo[2,3-b]pyrazine (45, RP91): mp 266.3° C.; IR 3138, 3050, 3025, 2928, 2858 cm$^{-1}$; $^1$H NMR δ (60 MHz, DMSO-d$_6$) 4.25 (s, 2H), 7.15 (s, 5H), 7.55 (s, 4H), 8.20 and 8.35 (2d, 1H each, J=3 Hz), 12.25 (bs, 1H). Anal. (C$_{19}$H$_{14}$N$_3$Cl) C, H, N.

6-(4-Methoxyphenyl)-7-methylcyclohexyl[5H]pyrrolo[2,3-b]pyrazine (46, RP98): mp 220.3° C.; IR 3434, 3135, 2921, 2850 cm$^{-1}$; $^1$H NMR δ (60 MHz, DMSO-d$_6$) 0.85-1.80 (m, 11H), 2.80 (d, 2H, J=6.5 Hz), 3.80 (s, 3H), 7.15 and 7.70 (2d, 2H each, J=8.2 Hz), 8.15 and 8.35 (2d, 1H each, J=2.5 Hz), 11.90 (bs, 1H). Anal. (C$_{20}$H$_{23}$N$_3$O) C, H, N.

6-(4-Chlorophenyl)-7-methylcyclohexyl[5H]pyrrolo[2,3-b]pyrazine (47, RP99): mp 203.5° C.; IR 3142, 3048, 2928, 2847 cm$^{-1}$; $^1$H NMR δ (60 MHz, DMSO-d$_6$) 0.80-1.75 (m, 11H), 2.80 (d, 2H, J=6.5 Hz), 7.65 (s, 4H), 8.20 and 8.40 (2d, 1H each, J=2.4 Hz), 12.10 (bs, 1H). Anal. (C$_{19}$H$_{20}$N$_3$Cl) C, H, N.

c—General method for the demethylation of methoxy-substituted 6-phenyl[5H]pyrrolo[2,3-b]pyrazines First, hydrobromic acid was redistilled over a trace of 50% hypophosphorus acid: 1 g for each 100 g of 48% hydrobromic acid. Methoxy compound (0.003 mol) was heated with hydrobromic acid (20 ml). After removal of the aqueous forerun, the temperature reaches 126° C. The time required for demethylation varies from 3-10 h. The excess of hydrobromic acid was removed under reduced pressure, and the crude product was crystallised from ethanol.

6-(2-Hydroxyphenyl)[5H]pyrrolo[2,3-b]pyrazine hydrobromide (11, RP109): mp 250° C. dec; IR 3419, 3354, 3090, 2710, 2641 cm$^{-1}$; $^1$H NMR δ (60 MHz, DMSO-d$_6$) 5.80 (s, 3H), 6.80-7.30 (m, 4H), 7.70-8.00 (m, 1H), 8.40 (bs, 3H), 12.85 (bs, 1H). Anal. (C$_{12}$H$_9$N$_3$O, HBr, H$_2$O) C, H, N.

6-(3-Hydroxyphenyl)[5H]pyrrolo[2,3-b]pyrazine hydrobromide (13, RP134): mp 258° C. dec.; IR 3448, 3137, 3085, 2700, 2630 cm$^{-1}$; $^1$H NMR δ (60 MHz, DMSO-d$_6$) 6.70-7.50 (m, 7H), 8.65 (bs, 2H), 13.45 (bs, 1H). Anal. (C$_{12}$H$_9$N$_3$O, HBr) C, H, N.

6-(4-Hydroxyphenyl) [5H]pyrrolo[2,3-b]pyrazine hydrobromide (15, RP26): mp 255° C. dec; IR 3448, 3176, 3060 cm$^{-1}$; $^1$H NMR δ (60 MHz, DMSO-d$_6$) 6.65-6.85 (m, 4H), 7.70 and 7.85 (2d, 2H each, J=8.2 Hz), 8.15 and 8.25 (2d, 1H each, J=3 Hz), 9.65 (s, 1H), 12.10 (bs, 1H). Anal. (C$_{12}$H$_9$N$_3$O, HBr, H$_2$O) C, H, N.

6-(4-Hydroxyphenyl)-7-methyl[5H]pyrrolo[2,3-b]pyrazine hydrobromide (28, RP96): mp 262° C. dec; IR 3465, 3143, 3090, 2796, 2759 cm$^{-1}$; $^1$H NMR δ (60 MHz, DMSO-d$_6$) 2.45 (s, 3H); 7.00 and 7.70 (2d, 2H each, J=8.2 Hz), 8.50 (bs, 2H), 9.80 (s, 2H), 13.00 (bs, 1H). Anal. (C$_{13}$H$_{11}$N$_3$O, HBr) C, H, N.

6-(4-Hydroxyphenyl)-7-propyl[5H]pyrrolo[2,3-b]pyrazine hydrobromide (33, RP132): mp 244° C. dec; IR 3187, 3100, 2965, 2873, 2798 cm$^{-1}$; $^1$H NMR δ (60 MHz, DMSO-d$_6$) 0.85 (t, 3H, J=7 Hz), 1.35-1.90 (m, 2H), 3.10-2.75 (m, 2H), 7.20 and 7.65 (2d, 2H each, J=8.2 Hz), 8.50 (s, 2H), 9.8 (s, 2H), 13.1 (s, 1H). Anal. (C$_{15}$H$_{15}$N$_3$O, HBr) C, H, N.

7-n-Butyl-6-(4-hydroxyphenyl)[5H] pyrrolo[2,3-b]pyrazine (39, RP107): mp 281.4° C.; IR 3134, 3100, 2946, 2924, 2867 cm$^{-1}$; $^1$H NMR δ (60 MHz, DMSO-d$_6$) 0.90 (t, 3H, J=7 Hz), 1.20-1.90 (m 4H), 2.90 (t, 2H, J=7.5 Hz), 6.95 and 7.60 (2d, 2H each, J=7 Hz), 8.15 and 8.30 (2d, 1H each, J=2.6 Hz), 9.80 (bs, 1H), 11.80 (bs, 1H). Anal. (C$_{16}$H$_{17}$N$_3$O) C, H, N.

6-(4-Hydroxyphenyl)-7-methylcyclopropyl[5H]pyrrolo [2,3-b]pyrazine hydrobromide (43, RP112): mp 260° C. dec; IR 3482, 3335, 3064, 2983 cm$^{-1}$; $^1$H NMR δ (60 MHz, DMSO-d$_6$) 1.60 (d, 4H, J=6 Hz), 2.00-2.60 (m, 3H), 2.90-3.60 (m, 4H), 7.05 and 7.90 (2d, 2H each, J=8.2 Hz), 8.55-8.80 (m, 2H), 13.45 (bs, 1H). Anal. (C$_{16}$H$_{15}$N$_3$O, HBr, H$_2$O) C, H, N.

B/ BIOCHEMISTRY

Biochemical Reagents

Sodium ortho-vanadate, EGTA, EDTA, Mops, β-glycerophosphate, phenylphosphate, sodium fluoride, dithiothreitol (DTT), glutathione-agarose, glutathione, bovine serum albumin (BSA), nitrophenylphosphate, leupeptin, aprotinin, pepstatin, soybean trypsin inhibitor, benzamidine, histone H1 (type III-S) were obtained from Sigma Chemicals. [γ-$^{32}$P]-ATP (PB 168) was obtained from Amersham. The GS-1 peptide has sequence SEQ ID No 1 YRRAAVPPSPSLSRHSSPHQSpEDEEE.

Buffers

Homogenization Buffer: 60 mM β-glycerophosphate, 15 mM p-nitrophehylphosphate, 25 mM Mops (pH 7.2), 15 mM EGTA, 15 mM MgCl$_2$, 1 mM DTT, 1 mM sodium vanadate, 1 mM NaF, 1 mM phenylphosphate, 10 μg leupeptin/ml, 10 μg aprotinin/ml, 10 μg soybean trypsin inhibitor/ml and 100 μM benzamidine.

Buffer A: 10 mM MgCl$_2$, 1 mM EGTA, 1 mM DTT, 25 mM Tris-HCl pH 7.5, 50 μg heparin/ml.

Buffer C: homogenization buffer but 5 mM EGTA, no NaF and no protease inhibitors.

Tris-Buffered Saline-Tween-20 (TBST): 50 mM Tris pH 7.4, 150 mM NaCl, 0.1% Tween-20.

Hypotonic Lysis Buffer (HLB): 50 mM Tris-HCl pH 7.4, 120 mM NaCl, 10% glycerol, 1% Nonidet-P40, 5 mM DTT, 1 mM EGTA, 20 mM NaF, 1 mM orthovanadate, 5 μM microcystin, 100 μg/ml each of leupeptin, aprotinin and pepstatin.

Kinase Preparations and Assays

Kinases activities were assayed in Buffer A or C (unless otherwise stated), at 30° C., at a final ATP concentration of 15 μM. Blank values were subtracted and activities calculated as pmoles of phosphate incorporated for a 10 min. incubation. The activities are usually expressed in % of the maximal activity, i.e. in the absence of inhibitors. Controls were performed with appropriate dilutions of dimethylsulfoxide. In a few cases phosphorylation of the substrate was assessed by autoradiography after SDS-PAGE.

GSK-3α/β was either purified from porcine brain or expressed in and purified from insect Sf9 cells. It was assayed, following a 1/100 dilution in 1 mg BSA/ml 10 mM DTT, with 5 μl 40 μM GS-1 peptide as a substrate, in buffer A, in the presence of 15 μM [γ-$^{32}$P] ATP (3,000 Ci/mmol; 1 mCi/ml) in a final volume of 30 μl. After 30 min. incubation at 30° C., 25 μl aliquots of supernatant were spotted onto 2.5×3 cm pieces of Whatman P81 phosphocellulose paper, and, 20 sec. later, the filters were washed five times (for at least 5 min. each time) in a solution of 10 ml phosphoric acid/liter of water. The wet filters were counted in the presence of 1 ml ACS (Amersham) scintillation fluid.

CDK1/cyclin B was extracted in homogenisation buffer from M phase starfish (*Marthasterias glacialis*) oocytes and purified by affinity chromatography on p9$^{CKShs1}$-sepharose beads, from which it was eluted by free p9$^{CKShs1}$. The kinase activity was assayed in buffer C, with 1 mg histone H1/ml, in the presence of 15 μM [λ-$^{32}$P] ATP (3,000 Ci/mmol; 1 mCi/ml) in a final volume of 30 μl. After 10 min. incubation at 30° C., 25 μl aliquots of supernatant were spotted onto P81 phosphocellulose papers and treated as described above.

CDK5/p25 was reconstituted by mixing equal amounts of recombinant mammalian CDK5 and p25 expressed in *E. coli* as GST (Glutathione-S-transferase) fusion proteins and purified by affinity chromatography on glutathione-agarose (p25 is a truncated version of p35, the 35 kDa CDK5 activator). Its activity was assayed in buffer C as described for CDK1/cyclin B.

Other kinases were expressed, purified and assayed as described previously (9), (10).

Results

Inhibitory-Effects of Aloisines on CDK1, CDK5 & GSK-3

Kinases were assayed as above described in the presence of increasing concentrations of aloisines. IC$_{50}$'s were calculated from the dose-response curves and are given in Table 1 hereinafter in μM.

TABLE 1

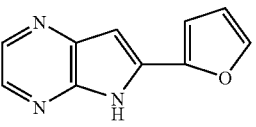

| N° | a | b | c | d | 7 | CDK1/cyclin B | CDK5/p25 | GSK-3 |
|---|---|---|---|---|---|---|---|---|
| 5 (RP7) | — | — | — | — | — | 5.00 | 4.00 | 2.30 |
| 10 (RP9) | $OCH_3$ | — | — | — | — | 20.00 | 23.00 | 3.30 |
| 11 (RP109) | OH | — | — | — | — | 2.50 | 3.00 | 6.50 |
| 12 (RP10) | — | $OCH_3$ | — | — | — | 13.00 | 10.00 | 3.20 |
| 13 (RP134) | — | OH | — | — | — | 2.50 | — | — |
| 14 (RP11) | — | — | $OCH_3$ | — | — | 2.00 | 4.00 | 1.10 |
| 15 (RP26) | — | — | OH | — | — | 1.20 | 1.00 | 1.20 |
| 16 (RP21) | — | $OCH_3$ | — | $OCH_3$ | — | 100.00 | >100.00 | 60.00 |
| 17 (RP16) | — | $OCH_3$ | $OCH_3$ | $OCH_3$ | — | 100.00 | >100.00 | 85.00 |
| 18 (RP76) | — | — | F | — | — | 2.30 | 1.00 | 1.90 |
| 19 (RP14) | — | — | Cl | — | — | 1.80 | — | — |
| 20 (RP15) | — | Cl | — | Cl | — | >100.00 | >100.00 | >100.00 |
| 21 (RP77) | — | — | Br | — | — | 4.00 | >100.00 | 6.00 |
| 22 (RP8) | — | — | $CF_3$ | — | — | 6.00 | >100.00 | 7.20 |
| 24 (RP78) | — | — | $CH_3$ | — | — | 3.00 | 10.00 | 2.60 |
| 23 (RP20) | — | — | CN | — | — | 3.00 | 13.00 | 4.80 |
| 26 (RP129) | — | — | $N(CH_3)_2$ | — | — | 20.00 | >100.00 | 12.00 |
| 27 (RP95) | — | — | $OCH_3$ | — | $CH_3$ | 0.30 | 0.80 | 0.46 |
| 29 (RP123) | — | $OCH_3$— | $OCH_3$ | — | $CH_3$ | 1.10 | 1.00 | 2.00 |
| 32 (RP127) | — | — | $OCH_3$ | — | $(CH_2)_2CH_3$ | 0.40 | 0.50 | 0.40 |
| 35 (RP126) | — | — | $OCH_3$ | — | $(CH_2)_3$—Cl | 1.30 | 3.00 | 2.50 |
| 36 (RP102) | — | — | $OCH_3$ | — | $CH(CH_3)_2$ | 1.00 | 2.00 | 0.50 |
| 34 (RP110) | — | — | $OCH_3$ | — | $CH_2$—CH=$CH_2$ | 1.00 | 2.00 | 0.60 |
| 38 (RP106) | — | — | $OCH_3$ | — | $(CH_2)_3$—$CH_3$ | 0.70 | 1.50 | 0.92 |
| 41 (RP111) | — | — | $OCH_3$ | — | $(CH_2)_6$—$CH_3$ | 7.00 | >100.00 | >10.00 |
| 42 (RP104) | — | — | $OCH_3$ | — | $CH_2$—$C_3H_5$ | 1.00 | >100.00 | 1.10 |
| 46 (RP98) | — | — | $OCH_3$ | — | $CH_2$—$C_6H_{11}$ | 5.00 | >100.00 | 6.80 |
| 31 (RP125) | — | — | O—$SO_2$—$N(CH_3)_2$ | — | $CH_3$ | 0.70 | 0.90 | 0.50 |
| 30 (RP80) | — | — | Cl | — | $CH_3$ | 0.40 | 5.00 | 1.70 |
| 37 (RP90) (aloisine B) | — | — | Cl | — | $CH(CH_3)_2$ | 0.85 | 13.00 | 0.75 |
| 40 (RP108) | — | — | Cl | — | $(CH_2)_3$—$CH_3$ | 0.20 | >100.00 | 5.90 |
| 45 (RP91) | — | — | Cl | — | $CH_2$—$C_6H_5$ | 40.00 | >100.00 | 6.80 |
| 44 (RP92) | — | — | — | — | $CH_2$—$C_6H_5$ | 2.00 | >100.00 | 1.00 |
| 47 (RP99) | — | — | Cl | — | $CH_2$—$C_6H_{11}$ | 10.00 | >100.00 | 8.00 |
| 28 (RP96) | — | — | OH | — | $CH_3$ | 0.25 | 0.20 | 0.52 |
| 33 (RP132) | — | — | OH | — | $(CH_2)_2CH_3$ | 25.00 | 1.20 | 1.80 |
| 39 (RP107) (aloisine A) | — | — | OH | — | $(CH_2)_3$—$CH_3$ | 0.15 | 0.20 | 0.65 |
| 43 (RP112) | — | — | OH | — | $CH_2$—$C_3H_5$ | 50.00 | >100.00 | 3.00 |

Structure activity relationship of aloisine-related compounds.

| N° | structure | CDK1/cyclin B | CDK5/p25 | GSK-3 |
|---|---|---|---|---|
| 1 (RP19) | 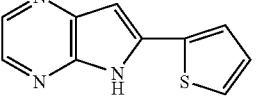 | 12 | 9.30 | 15 |
| 2 (RP6) | 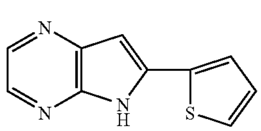 | 7.00 | 2.00 | 1.20 |
| 3 (RP128) | 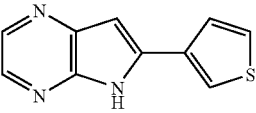 | 2.30 | 1.00 | 0.80 |

TABLE 1-continued

[Core structure: pyrrolo[2,3-b]pyrazine with numbered positions 1-N, 2, 3, 4-N, 5-NH, 6, 7 and phenyl ring with positions a, b, c, d, e]

| | Structure | | | |
|---|---|---|---|---|
| 4 (RP13) | pyrrolopyrazine-2-pyridyl | 21.00 | 53.00 | 15.00 |
| 6 (RP17) | pyrrolopyrazine-1-naphthyl | >100.00 | 80.00 | 27.00 |
| 9 (RP124) | pyrrolopyrazine-(cyclopropyl, 4-Cl-phenyl) | 30.00 | 100.00 | 1.00 |
| 49 (RP130) | pyrrolopyrazine-7-CH₃-(cyclopropyl, 4-Cl-phenyl) | 25.00 | 100.00 | 18.00 |
| 25 (RP122) | pyrrolopyrazine-phenyl-CHO | 8.00 | 15.00 | 20.00 |
| 8 (RP18) | 2-methyl-pyrrolopyrazine-phenyl | 69.00 | 100.00 | >100.00 |
| 48 (RP22) | N-methyl-pyrrolopyrazine-phenyl | 100.00 | 7.00 | >100.00 |

FIG. 1 gives the results obtained in the presence of increasing concentrations of aloisines A and B. Activity is presented as % of maximal activity, i.e. measured in the absence of inhibitors.

Said results show that the aloisines of the invention are potent inhibitors of CDKs and GSK-3 and for most of them in the submicromolar range.

Aloisine is a Competitive Inhibitor of ATP Binding

Figure 2:
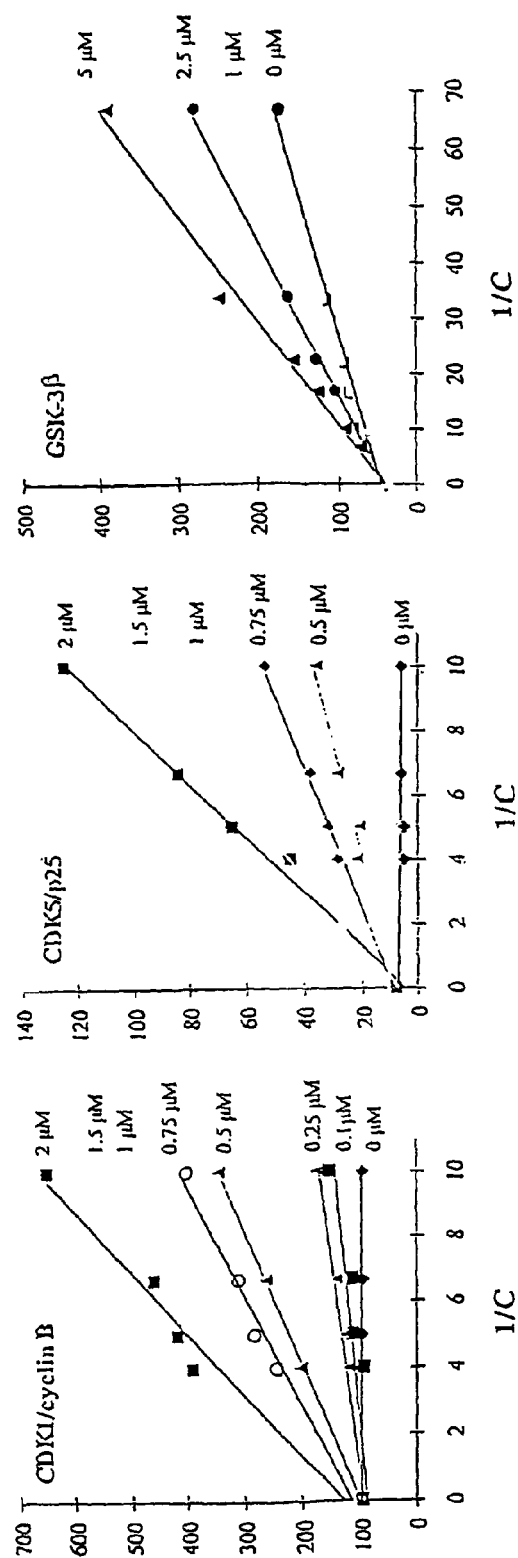
FIG. 2A; CDK5/p25.
FIG. 2B, and GSK-3β.
FIG. 2C), FIG. 3, stereo view of the interactions between aloisine B and the CDK2 ATP binding site, FIGS. 4A to 4E, reversible inhibition of exponential cell growth by aloisine A, and FIG. 5, the comparison of the effects of aloisine A on G0/G1 (A, B, C) and G2/M (D, E, F)

To investigate the mechanism of aloisine action, kinetic experiments were performed by varying both ATP levels and aloisine A concentrations. Double reciprocal plots of kinetic data from assays of CDK1/cyclin B (A), CDK5/p25 (B) and GSK-3β (C) kinase activities at different concentrations of aloisine A are given on FIG. 2. Enzyme activities were assayed as described in the Experimental section. ATP concentrations in the reaction mixture varied from 0.1 to 0.25 mM (CDK1 and CDK5) or 0.015 to 0.15 mM (GSK-3☐). The concentrations of histone H1 (A, B) and GS-1 (C) were kept constant at 0.7 mg/ml and 6.7 µM, respectively.

The data demonstrate that aloisine A acts as a competitive inhibitor for ATP. These results are in complete agreement with the localization of aloisine B within the ATP binding pocket of CDK2 (see below).

Crystallography

Expression, Purification and Crystallisation of Human CDK2

Human CDK2 was expressed from a recombinant baculovirus in Sf9 insect cells and purified. Monomeric unphosphorylated CDK2 crystals were grown as previously described in (11).

X-ray Crystallography Data Collection and Processing

The CDK2-aloisine B dataset was collected from a monomeric CDK2 crystal soaked for 60 h in 1 mM aloisine B in 1× mother liquor solution (50 mM ammonium acetate, 10% PEG3350, 15 mM NaCl, 100 mM HEPES, pH7.4) plus 5% DMSO. Data was collected on beamline X-RAY DIFFRACTION at the Elettra Light Source at 100K after the crystal had been transferred briefly to cryo-protectant (mother liquor adjusted to contain 20% glycerol). The images were integrated with the MOSFLM package (12) and reflections were subsequently scaled and merged using SCALA (13). Subsequent data reduction and structure refinement were pursued through programs of the CCP4 suite.

Aloisine B occupies the CDK2 ATP binding site and makes two hydrogen bonds to the CDK2 backbone within the hinge sequence that links the two lobes of the kinase. CDK2 is drawn in ribbon representation and colour-ramped from blue through to red starting at the N-terminus. The N-terminal lobe is dominated by a 5-stranded anti-parallel β-sheet and the C-terminal lobe is predominantly α-helical. Aloisine B is drawn in ball and stick mode bound at the ATP-binding site which lies in the cleft between the two domains. Aloisine B carbon atoms are coloured cyan, nitrogen atoms blue and the chlorine atom is drawn in yellow.

Figure 3:
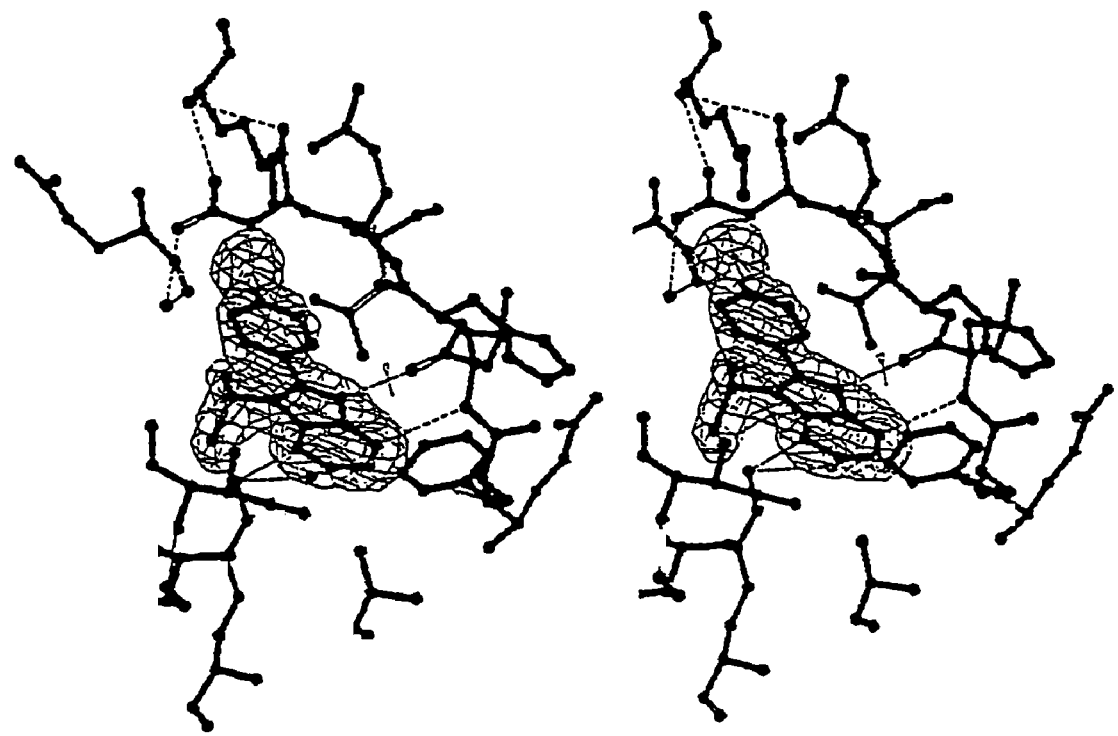

Unlike the natural ligand, ATP, aloisine B does not interact with the backbone oxygen of Glu81, but instead accepts and donates a hydrogen bond respectively from the backbone nitrogen and oxygen atoms of Leu 83 (FIG. 3) residues that lie within 4 Å of the bound aloisine B molecule are drawn in ball and stick mode. Aloisine B carbon atoms are drawn in cyan and those of CDK2 in green. Oxygen atoms are coloured red, nitrogen atoms are blue and the chlorine atom is drawn in yellow. Dotted lines represent hydrogen bonds (dO—>N or dN—O<3.4 Å) between aloisine B and the backbone nitrogen and oxygen atoms of Leu 83. The Figure also includes (2Fo-Fc)α-calc electron density for aloisine B calculated at the end of refinement using map coefficients output from REFMAC with resolution between 20 and 1.9 Å. The map is contoured at a level of 0.19e-Å$^{-3}$ corresponding to 1.0 times the r.m.s. deviation of the map from its mean value.

This hydrogen-bonding pattern has previously been observed in the structures of monomeric CDK2 in complex with olomoucine, roscovitine, purvalanol B, OL567 and H717. The CDK2 ATP-binding site is tolerant of a number of positions for the planar heterocyclic ring systems which are a characteristic of the CDK inhibitors identified to date. The position of the aloisine B fused ring system within the CDK2 ATP binding site most closely resembles that of indirubin-5-sulphonate and oxindole-3. However, being smaller than indirubin-5-sulphonate and in a different orientation to oxindole-3, aloisine B does not fill the back of the ATP-binding cleft and form an equivalent edge-to-ring stacking interaction with the side-chain of Phe 80.

Aloisines, Kinase Selectivity

Aloisine A, the most active aloisine so far, was tested for selectivity on 26 highly purified kinases. Kinase activities were assayed with appropriate substrates (for example histone H1, casein, myelin basic protein and peptides), with 15 µM ATP and in the presence of increasing concentrations of aloisine A. $IC_{50}$ values were estimated from the dose-response curves and are presented in Table 3.

TABLE 3

Kinase inhibition selectivity of aloisine A.

| Protein Kinases | $IC_{50}$ (µM) |
|---|---|
| CDK1/cyclin B | 0.15 |
| CDK2/cyclin A | 0.12 |
| CDK2/cyclin E | 0.40 |
| CDK4/cyclin D1 | >100.00 |
| CDK5/p35 | 0.16 |
| erk1 | 18.00 |
| erk2 | 22.00 |

TABLE 3-continued

Kinase inhibition selectivity of aloisine A.

| Protein Kinases | $IC_{50}$ (µM) |
|---|---|
| c-raf | >100.00 |
| MAPKK | >100.00 |
| c-Jun N-terminal kinase | 3.3-10 |
| protein kinase C α | >100.00 |
| protein kinase C β1 | >100.00 |
| protein kinase C β2 | >100.00 |
| protein kinase C γ | >100.00 |
| protein kinase C δ | >100.00 |
| protein kinase C ε | >100.00 |
| protein kinase C η | >100.00 |
| protein kinase C ζ | >100.00 |
| cAMP-dependent protein kinase | 100.00 |
| cGMP-dependent protein kinase | 100.00 |
| GSK3-α | 0.50 |
| GSK3-β | 1.50 |
| Casein kinase 1 | >100.00 |
| Casein kinase 2 | >100.00 |
| Insulin receptor tyrosine kinase | 60.00 |
| PIM 1 | >10.00 |

Most kinases tested were poorly or not inhibited ($IC_{50}$>10 µM). However, two families of kinases, GSK-3α/β and CDKs were strongly sensitive to aloisine A ($IC_{50}$'s of 0.65 and 0.15 µM, respectively) (FIG. 1; Table 3). Among the CDKs, CDK1, CDK2 and CDK5, but not CDK4 were inhibited by aloisine A. This is reminiscent of other CDK inhibitors, such as purines, hymenialdisine, paullones, and indirubins, which inhibit CDK1/2/5 but have much less effect on or not CDK4/6. Although aloisines appear to be remarkably specific to CDKs and GSK-3, the actual spectrum of their intracellular targets remains to be identified. For this purpose we are currently designing an immobilized aloisine matrix to purify aloisine-binding proteins by the affinity chromatography method described for purines and paullones.

C/ CELL BIOLOGY

Reagents

Penicillin, streptomycin, nocodazole, insulin, transferrin, progesterone, putrescine, sodium selenite, 3-(4,5-dimethylthiazol-2-yl)-2,5-diphenyltetrazolium-bromide (MTT), RNAse A, propidium iodide were purchased from Sigma.

Cell Cultures

Clonal human NT2 teraterocarcinoma cells were obtained from Stratagene (La Jolla, Calif.) and grown in Dulbecco's Modified Eagle Medium: Nutrient Mixture F-12 with 2 mM L-Glutamine (BIO WHITTAKER) supplemented with 5% FCS and containing penicillin (20 UI/ml) and streptomycin (20 µg/ml) at 37° C., in a humidified atmosphere containing 5% $CO_2$ in air.

NT2 Differentiation

Differentiation of NT2 cells to hNT cells was induced according to the method of Pleasure et al. (17) modified by Soulié et al. Briefly, after the second replating, cells were cultured in serum-free medium with a combination of mitotic inhibitors (1 µM cytosine arabinoside, 10 µM fluorodeoxyuridine and 10 µM uridine) and a mixture of salt and hormones (25 µg insulin/ml, 100 µg transferrin/ml, 20 nM progesterone, 60 µM putrescine and 30 nM sodium selenite) for 5 days before treatment.

Treatment with Aloisine

Exponentially growing cells were incubated for 24 h with aloisine A (stock solution dissolved in dimethylsulfoxide). Nocodazole treatment of cells was performed at a concentration of 0.04 µg nocodazole/ml of medium for 24 h. Following the nocodazole treatment, cells were washed twice with fresh medium and cultured with or without aloisine A for 24 h. To perform serum deprivation, cells were maintained in serum-free medium for 40 h. Following serum deprivation, cells were washed twice and cultured in fresh serum-containing medium with or without aloisine A for 40 h.

Cell Viability Assay

To quantify the toxicity of aloisine A on NT2 cells and hNT human neurons, the inhibition of cellular reduction of MTT to MTT formazan was measured according to Saillé et al. Following aloisine A exposure, cells were incubated with 0.5 mg MTT/ml fresh medium at 37° C. for 1 hour. The formazan products were dissolved in DMSO and quantified by measurement of the absorbance at 562 nm.

Cell Cycle Analysis by Flow Cytometry

Cells were trypsinised, collected by centrifugation and fixed in cold 70% ethanol for at least 4 h. Fixed cells were washed in PBS, incubated with 10 μg RNAse A/ml and stained with 25 μg propidium iodide/ml for 1 h at 37° C. The stained cells were then analysed for cell cycle distribution on a FACSort flow cytometer (Becton Dickinson). Cell cycle analyses were performed multiCYCLE (18).

Figure 4:
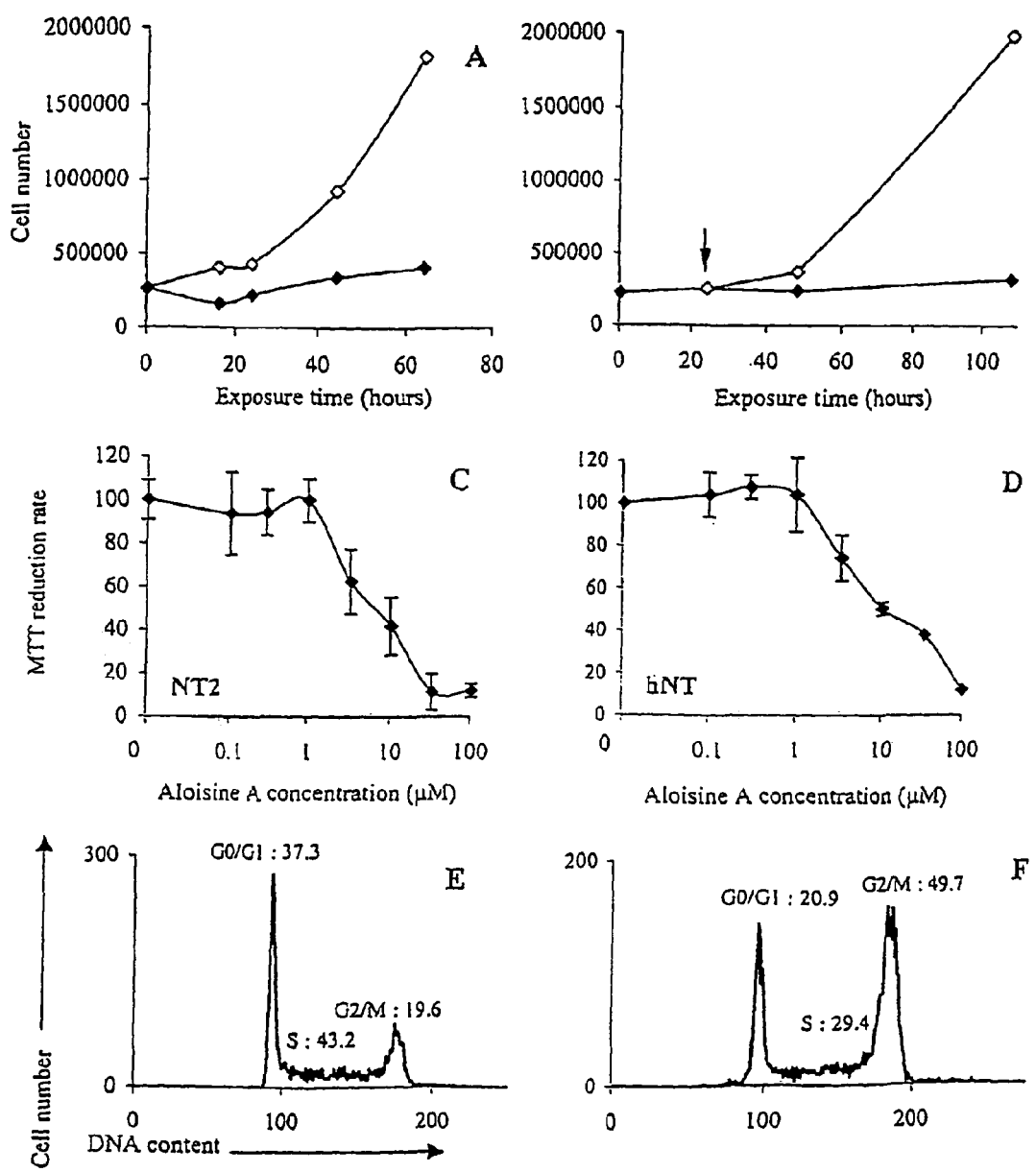

The effect of aloisine A on the cell cycle distribution was investigated for NT2 cells by flow cytometry. Unsynchronised cells (FIG. 4E) were exposed to 20 μM aloisine A for 40 h (FIG. 4F). The proliferation arrest induced by aloisine A in exponentially growing cells was clearly accompanied by an accumulation in G2/M phase. No signs of apoptosis were detectable, confirming the lack of apparent toxicity observed before.

The effects of aloisine A on NT2 cells synchronized either in G0/G1 by serum deprivation or in G2/M by nocodazole treatment was also investigated. The results are given on FIG. 4: the cell cycle phase distribution was analysed by flow cytometry following propidium iodide staining. (A, B, C). NT2 cells were synchronized by serum deprivation for 24 h (A), then cultured for 40 h in fresh medium without (B) or with 20 μM aloisine A (C). (D, E, F). NT2 cells were synchronized by nocodazole treatment (0.2 μg/ml) for 24 h (D), then cultured for 40 h in fresh medium without (E) or with 20 μM aloisine A (F).

Figure 5:
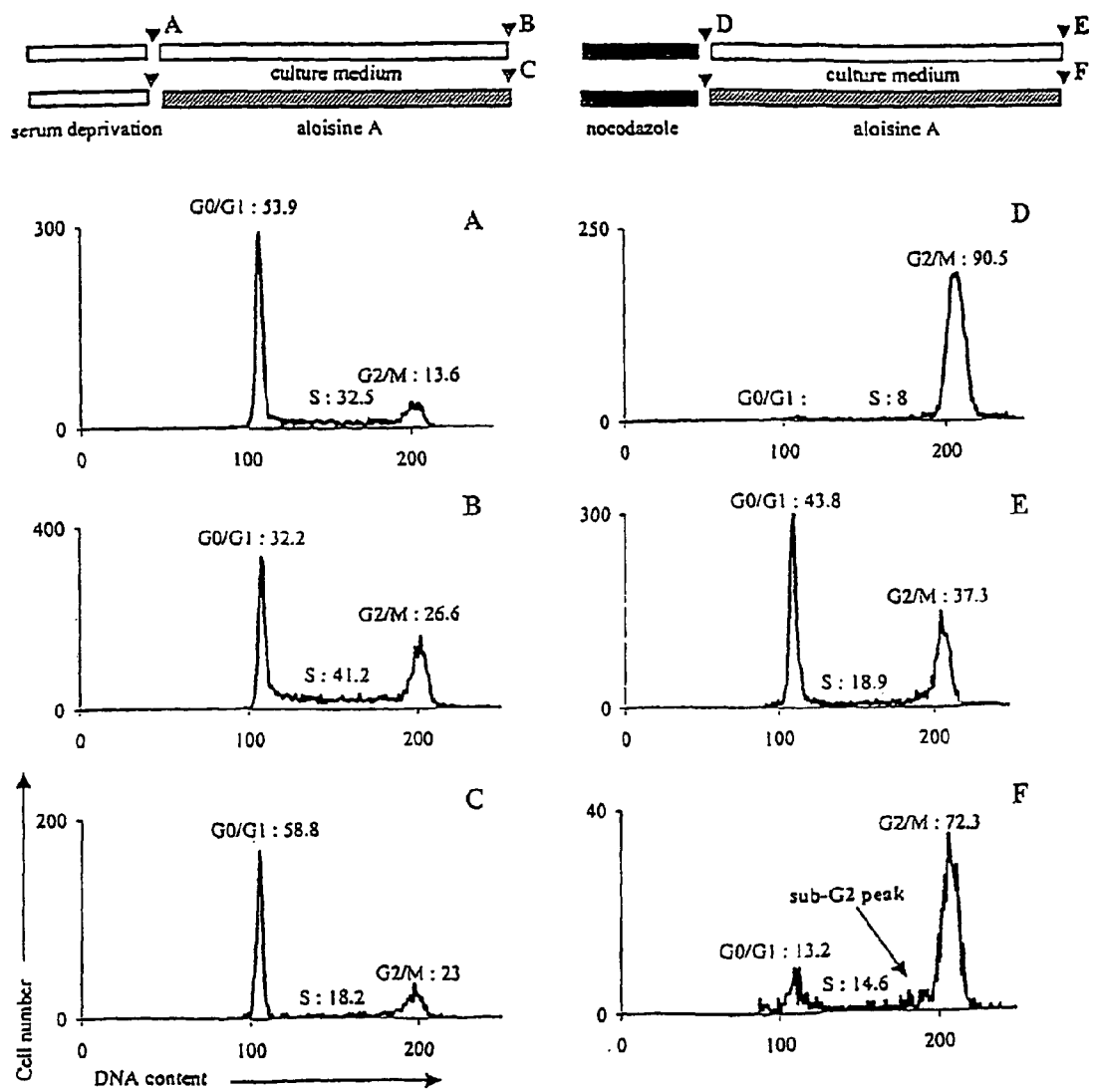

Serum deprivation for 24 h lead to a significant increase of cells in G0/G1 (FIG. 5A). Cells were then re-exposed to a serum-enriched media for 40 h in the absence (FIG. 5B) or presence (FIG. 5C) of 20 μM aloisine A. Aloisine A-treated cells remained essentially in G0/G1, with a small additional accumulation of G2/M cells, most probably derived from the initial S phase sub-population (FIG. 5C). Control cells redistributed in a classical cell cycle pattern (FIG. 5B). Nocodazole treatment for 24 h lead to a massive accumulation of cells in G2/M (FIG. 5D). Cells were then washed to remove nocodazole and incubated for 40 h in the absence (FIG. 5E) or presence (FIG. 5F) of 20 μM aloisine A. 40 h after nocodazole withdrawal, control cells redistributed in the various cell cycle phases (FIG. 8E). In contrast, the majority of cells exposed to aloisine A after nocodazole treatment remained in G2/M (FIG. 5F), precluding the increase in G1/G0 seen in control cells. A small sub-G2-peak may indicate a minor onset of apoptotic cell death.

All together these data indicate that aloisine A has antiproliferative properties and that it is able to block both the exit from G0/G1 and the exit from G2/M, suggesting the existence of several intracellular targets. A G1 arrest correlates with aloisine A's high potency against CDK2/cyclin E. The inability to enter S phase might also be result from inhibition of GSK-3, a kinase known to be involved in cyclin D1 degradation. The G2/M arrest correlates well with the potency of aloisine A against CDK1/cyclin B.

REFERENCES

1. Meijer, L. Cyclin-dependent kinases inhibitors as potential anticancer, anti-neurodegenerative, anti-viral and anti-parasitic agents. *Drug Resistance Update* 2000, 3, 83-88.
2. Toogood, P. L. Cyclin-dependent kinase inhibitors for treating cancer. *Med. Res. Rev.* 2001, 21, 487-498.
3. Gray, N.; Détivaud, L.; Doerig, C.; Meijer, L. ATP-site directed inhibitors of cyclin-dependent kinases. *Curr. Med. Chem.* 1999, 6, 859-876.
4. Fischer, P. M.; Lane, D. P. Inhibitors of cyclin-dependent kinases as anti-cancer therapeutics. *Curr. Med. Chem.* 2000, 7, 1213-1245.
5. Pestell, R.; Mani, S.; Wange, C.; Wu, K.; Francis, R. Cyclin-dependent kinase inhibitors: novel anticancer agents. *Expert Opin. Investig. Drugs* 2000, 9, 1849-1870.
6. Rosiana, G. R.; Chang, Y. T. Targeting hyperproliferative disorders with cyclin dependent kinase inhibitors. *Exp. Opin. Ther. Patents* 2000, 10, 1-16.
7. Sielecki, T. M.; Boylan, J. F.; Benfield, P. A.; Trainor, G. L. Cyclin-dependent kinase inhibitors: useful targets in cell cycle regulation. *J. Med. Chem.* 2000, 43, 1-18.
8. Kaubisch, A.; Schwartz G. K. Cyclin-dependent kinase and protein kinase C inhibitors: a novel class of antineoplastic agents in clinical development. *Cancer J.* 2000, 6, 192-212.
9. Meijer, L.; Borgne, A.; Mulner, O.; Chong, J. P. J.; Blow, J. J.; Inagaki, N.; Inagaki, M.; Delcros, J. G.; Moulinoux, J. P. Biochemical and cellular effects of roscovitine, a potent and selective inhibitor of the cyclin-dependent kinases cdc2, cdk2 and cdk5. *Eur. J. Biochem.* 1997, 243, 527-536.
10. Meijer, L.; Thunissen, A. M. W. H.; White, A.; Garnier, M.; Nikolic, M.; Tsai, L. H.; Walter, J.; Cleverley, K. E.; Salinas, P. C.; Wu, Y. Z.; Biernat, J.; Mandelkow, E. M.; Kim, S.-H.; Pettit, G. R. Inhibition of cyclin-dependent kinases, GSK-3β and casein kinase 1 by hymenialdisine, a marine sponge constituent. *Chem. & Biol.* 2000, 7-51-63.
11. Lawrie, A. M.; Noble, M. E.; Tunnah, P.; Brown, N. R.; Johnson, L. N.; Endicott, J. A. Protein kinase inhibition by staurosporine revealed in details of the molecular interaction with CDK2. *Nature Structural Biol.* 1997, 4, 796-800.
12. Leslie, A. G. W. *Joint CCP4 and ESF-EAMCB Newsletter on Protein Crystallography.* 1992, vol. 26.
13. CCP4. The CCP4 (Collaborative Computational Project Number 4) suite: Programs for protein crystallography. *Acta Cryst. D,* 1994, 50, 760-763.
14. Navaza, J. AMoRe: An automated package for molecular replacement. *Acta. Cryst.,* 1994, A50, 157-163.
15. Murshudov, G. N.; Vagin, A. A.; and Dodson, E. J. Refinement of macromolecular structures by the maximum-likelihood method. *Acta Cryst. D,* 1997, 53, 240-255.
16. Jones, T. A., Zou, J. Y., Cowan, S. W., Kjeldgaard, M. Improved methods for building protein models in electron density maps and the location of errors in these models. *Acta Cryst. A,* 1991, 47, 110-119.
17. Pleasure, S. J.; Page, C.; Lee, V. M. Y. Pure, post-mitotic polarized human neurons derived from NT2 cells provide a system for expressing exogenous proteins in terminally differentiated neurons. *J. Neurosci.* 1992, 12, 1802-1815.
18. Damiens, E.; Baratte, B.; Marie, D.; Eisenbrand, G.; and Meijer, L. Anti-mitotic properties of indirubin-3'-monoxime, a CDK/GSK-3 inhibitor: induction of endoreplication following prophase arrest. *Oncogene,* 2001, 20, 3786-3797.

The invention claimed is:

1. A Pyrrolo[2,3b]-pyrazine derivative having the general formula (I):

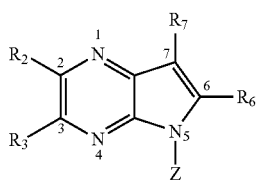

wherein:
R2 and R3 are identical or different, and represent H, C1-C6 alkyl, said alkyl being a straight or branched-chain alkyl, which can be substituted,
R6 is a cycloalkyl, said cycloalkyl being optionally substituted by an aryl group which can also be substituted,
R7 is H, C1-C6 alkyl, (alk.)$_n$-hal., CH$_2$—CH=CH$_2$, CH$_2$-cycloalkyl, CH$_2$—Ar, with "alk." being a C1-C6 alkylene group, n being 1-6,
Z is CH$_3$.

2. The pyrrolo[2,3b]-pyrazine derivative of claim 1, wherein the Cycloalkyl group is a C3-C6 cycloalkyl.

3. The pyrrolo[2,3b]-pyrazine derivative of claim 1, wherein the substitutions groups are independently selected from halogen, OH, NH$_2$, N(H, alkyl), N(alkyl)$_2$, O-alkyl, COOH, COO-alkyl, CONH$_2$, CON(H, alkyl), CON(alkyl)$_2$, NHCONH$_2$, NHCON(H, alkyl), NHCON (alkyl)$_2$, N(alkyl) CONH$_2$, N(alkyl)CON(H, alkyl), N(alkyl)CON(alkyl)$_2$, alkoxy, CN, O—SO$_2$—NH$_2$, O—SO$_2$—N(H, alkyl), —O—SO$_2$—N (alkyl)$_2$, SH, S-alkyl.

4. A pharmaceutical composition comprising an effective amount of at least one derivative of claim 1 as active principle, in association with a pharmaceutically acceptable carrier.

5. The pharmaceutical composition of claim 4 for treating Alzheimer's disease.

6. The pharmaceutical composition of claim 4, in a form to be administered in one of the following forms: orally, topically, injection intravenously, injection subcutaneously, injection intraperitoneally, or rectally.

7. The pharmaceutical composition of claim 6, for administration by the oral route comprising 100 to 1000 mg of active principle per dose unit.

8. The pharmaceutical compositions of claim 6 under injectable forms, comprising 100 to 1000 mg of active principle per dose unit.

9. The pharmaceutical composition of claim 6, for administration by the oral route comprising 300 to 600 mg of active principle per dose unit.

10. The pharmaceutical composition of claim 6 under injectable forms, comprising 300 to 600 mg of active principle per dose unit.

11. The pyrrolo[2,3b]-pyrazine derivative of claim 3, wherein the halogen is selected independently from F, Cl, Br, I and CF$_3$.

* * * * *

SEQUENCE LISTING

```
<160> NUMBER OF SEQ ID NOS: 1

<210> SEQ ID NO 1
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)
<223> OTHER INFORMATION: Phosphorylated-Ser

<400> SEQUENCE: 1

Tyr Arg Arg Ala Ala Val Pro Pro Ser Pro Ser Leu Ser Arg His Ser
  1               5                  10                  15

Ser Pro His Gln Ser Glu Asp Glu Glu Glu
             20                  25
```